(12) United States Patent
Kuhnreich

(10) Patent No.: US 12,326,378 B2
(45) Date of Patent: Jun. 10, 2025

(54) INJURY DETECTION WEARABLE SYSTEM

(71) Applicant: XMETIX LTD., Nazareth (IL)

(72) Inventor: Irad Kuhnreich, Haifa (IL)

(73) Assignee: XMETIX LTD., Nazareth (IL)

( * ) Notice: Subject to any disclaimer, the term of this patent is extended or adjusted under 35 U.S.C. 154(b) by 261 days.

(21) Appl. No.: 18/012,932

(22) PCT Filed: Jun. 24, 2021

(86) PCT No.: PCT/IL2021/050777
§ 371 (c)(1),
(2) Date: Dec. 25, 2022

(87) PCT Pub. No.: WO2021/260704
PCT Pub. Date: Dec. 30, 2021

(65) Prior Publication Data
US 2023/0266187 A1 Aug. 24, 2023

Related U.S. Application Data

(60) Provisional application No. 63/043,907, filed on Jun. 25, 2020.

(51) Int. Cl.
*G01L 5/00* (2006.01)
*A61B 5/00* (2006.01)
*G16H 40/67* (2018.01)

(52) U.S. Cl.
CPC .......... *G01L 5/0052* (2013.01); *A61B 5/4836* (2013.01); *A61B 5/6804* (2013.01); *G16H 40/67* (2018.01)

(58) Field of Classification Search
CPC .......... G01L 5/00; G01L 5/02; G01L 5/0052; G16H 40/00; G16H 40/67; A61B 5/4836; A61B 5/6804
See application file for complete search history.

(56) References Cited

U.S. PATENT DOCUMENTS

| 4,106,002 A | 8/1978 | Hogue, Jr. |
| 4,655,227 A | 4/1987 | Gracovetsky |

(Continued)

FOREIGN PATENT DOCUMENTS

| CN | 201408495 Y | 2/2010 |
| CN | 203059823 U | 7/2013 |

(Continued)

OTHER PUBLICATIONS

Nicholas, N. C., & Welsch, J. R. (2004). Institute for Non-Lethal Defense Technologies Report: Ballistic Gelatin. Penn State Applied Research Laboratory. Available online: [https://apps.dtic.mil/sti/tr/pdf/ADA446543.pdf].

(Continued)

*Primary Examiner* — Nguyen Q. Ha
(74) *Attorney, Agent, or Firm* — The Roy Gross Law Firm, LLC; Roy D. Gross

(57) ABSTRACT

A system comprising: a wearable element designed to be worn on a body region of a subject; an array of sensors arranged at specified locations, attached to the wearable element; and a detection module in communication with each of the sensors in the array and configured to determine a parameter indicative of an injury to the body region, based on the signal. The parameter indicative of an injury to the body region may include at least in part, on at least one of: (i) an impact event associated with said subject calculated from the signal, (ii) a location of each of the at least one of the sensors relative to the body region, and a timing of the generating in the signal generated by the at least one sensor.

19 Claims, 10 Drawing Sheets

(56) References Cited

U.S. PATENT DOCUMENTS

| | | | |
|---|---|---|---|
| 4,671,290 | A | 6/1987 | Miller et al. |
| 5,715,821 | A | 2/1998 | Faupel |
| 6,198,394 | B1 | 3/2001 | Jacobsen et al. |
| 6,800,007 | B2 | 10/2004 | Calkin |
| 7,371,403 | B2 | 5/2008 | McCarthy et al. |
| 7,981,135 | B2 | 7/2011 | Thorpe |
| 8,366,740 | B2 | 2/2013 | McEwen et al. |
| 8,403,846 | B1 | 3/2013 | Cienfuegos |
| 8,460,003 | B2 | 6/2013 | Bevan et al. |
| 8,465,514 | B1 | 6/2013 | Rose |
| 8,668,924 | B2 | 3/2014 | McCarthy et al. |
| 8,740,305 | B2 | 6/2014 | Greenwood |
| 8,915,118 | B2 | 12/2014 | Russell et al. |
| 9,107,592 | B2 | 8/2015 | Litt et al. |
| 9,173,660 | B2 | 11/2015 | Smith et al. |
| 9,600,995 | B2 | 3/2017 | Gaidar et al. |
| 9,687,195 | B2 | 6/2017 | Sims et al. |
| 9,730,704 | B2 | 8/2017 | Rose et al. |
| 10,136,903 | B2 | 11/2018 | Lynch et al. |
| 11,471,112 | B2 * | 10/2022 | Gruentzig .......... A61B 17/1325 |
| 2006/0281979 | A1 | 12/2006 | Kim et al. |
| 2008/0243173 | A1 | 10/2008 | Thorpe |
| 2010/0234877 | A1 | 9/2010 | Pienkowski et al. |
| 2010/0324455 | A1 | 12/2010 | Rangel et al. |
| 2011/0099682 | A1 | 5/2011 | Earley |
| 2014/0234166 | A1 | 8/2014 | Erickson |
| 2014/0320342 | A1 | 10/2014 | Parker et al. |
| 2015/0338926 | A1 | 11/2015 | Park et al. |
| 2016/0120471 | A1 * | 5/2016 | Hexels ................ F41J 5/06 600/587 |
| 2017/0035369 | A1 | 2/2017 | Miller et al. |
| 2017/0049164 | A1 | 2/2017 | Gruentzig |
| 2017/0127734 | A1 | 5/2017 | Roberts et al. |
| 2018/0214161 | A1 | 8/2018 | Carabajal |

FOREIGN PATENT DOCUMENTS

| | | |
|---|---|---|
| CN | 207850583 U | 9/2018 |
| CN | 109090730 A | 12/2018 |
| EP | 1731048 A1 | 12/2006 |
| EP | 2156197 B1 | 9/2010 |
| JP | 2005503197 A | 2/2005 |
| JP | 3159768 U | 6/2010 |
| JP | 5775202 B2 | 9/2015 |
| KR | 100763617 B1 | 10/2007 |
| KR | 20150100855 A | 9/2015 |
| WO | 2005046433 A2 | 5/2005 |
| WO | 2007101141 A3 | 1/2008 |
| WO | 2010068573 A1 | 6/2010 |
| WO | 2010105053 A2 | 9/2010 |
| WO | 2013084912 A1 | 6/2013 |
| WO | 2014137302 A1 | 9/2014 |
| WO | 2014204109 A1 | 12/2014 |
| WO | 2018054380 A1 | 3/2018 |
| WO | 2018108924 A1 | 6/2018 |
| WO | 2018213615 A2 | 11/2018 |

OTHER PUBLICATIONS

Stevenson T, Carr DJ, Stapley SA. The effect of military clothing on gunshot wounding patterns in gelatine. Int J Legal Med. Jul. 2019;133(4):1121-1131. doi: 10.1007/s00414-018-1972-8. Epub Nov. 28, 2018. PMID: 30488352; PMCID: PMC6570663.

Gaylord, S., Blair, R., Courtney, M. & Courtney, A. (2013). Bullet Retarding Forces in Ballistic Gelatin by Analysis of High Speed Video. https://doi.org/10.48550/arXiv.1305.5215.

PCT International Search Report for International Application No. PCT/IL2021/050777, mailed Oct. 21, 2021, 5pp.

PCT Written Opinion for International Application No. PCT/IL2021/050777, mailed Oct. 21, 2021, 5pp.

PCT International Preliminary Report on Patentability for International Application No. PCT/IL2021/050777, issued Dec. 13, 2022, 6pp.

* cited by examiner

INJURY DETECTION WEARABLE SYSTEM

CROSS-REFERENCE TO RELATED APPLICATIONS

This application is a National Phase of PCT Patent Application No. PCT/IL2021/050777 having International filing date of Jun. 24, 2021, which claims the benefit of priority of U.S. Provisional Application No. 63/043,907, filed on Jun. 25, 2020, and titled "INJURY DETECTION WEARABLE SYSTEM", the contents of which are all incorporated herein by reference in their entirety.

FIELD OF THE INVENTION

Embodiments of the present invention relate generally to the field of electronic systems and, more particularly, to a wearable electronic system.

BACKGROUND

Various types of sensing systems have been incorporated in wearable garments for monitoring various physiological parameters of the wearer for applications in the areas of recreation, sport, combat, diagnostics, and medical treatment.

In medical and combat-related applications, wearable impact detection systems may provide for detecting impacts to a body, and especially impacts which might cause injury, and thus increase survivability of the soldier on the battlefield and facilitate more rapid triage for the combat medic.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In accordance with some embodiments of the present invention, a system and method are provided for identifying an injury and prioritizing medical care administered to an injured subject using the system. The system and method facilitate obtaining quick and accurate information relating to a parameter (e.g., a type and/or severity) of an injury sustained by the user typically under combat in a battlefield setting.

In accordance with some embodiments of the present invention, a wearable system is provided comprising, a wearable element designed to be worn on a body region of a subject, an array of sensors at specified locations, attached to the wearable element. The wearable element is typically placed in close contact with the skin of the user at the body region such that impact to the sensors is indicative of damage to the skin of the user which in turn is indictive of damage to internal organs and blood vessels underlying the skin at the specified locations. The wearable system further comprises a detection module in communication with each one of the sensors in the array. The detection module receives signals generated by each of the sensors and monitors the signals to detect a change that may occur in the signals in response to impact to the sensor when the user suffers an injury. The change in the signal is typically a degree of loss of the signal which may include a reduction in the signal or complete loss of the signal (i.e., no signal). The detection module is configured to determine a parameter indicative of the injury suffered by the user (e.g., a type and/or severity of the injury) based, at least in part on at least one of: the change in the signal generated by at least one sensor, a location of the at least one sensor relative to the body region, and a timing of the detected change in the signal.

For some embodiments, the type of injury determined by the detection module typically includes blast wave trauma, penetration trauma (including perforating trauma), amputation, and blunt force trauma.

For some embodiments, an output is generated based on the detection module determining the parameter indicative of the injury, informing medical staff of the type of the injury, thereby facilitating remote assessing the user's medical condition and prioritizing the need of the user for medical care with respect to others. Such information contributes to reduced mortality and morbidity rates among injured soldiers by enabling both timely and appropriate treatment in accordance with the type and severity of the injury.

There is therefore provided in accordance with some embodiments of the present invention, a system comprising: a wearable element designed to be worn on a body region of a subject, an array of sensors arranged at specified locations, attached to the wearable element; and a detection module in communication with each of said sensors in the array and configured to determine a parameter indicative of an injury to said body region, based on at least one signal generated by at least one of said sensors.

In some embodiments, the parameter indicative of the injury, is at least one of: (i) an impact event associated with said subject calculated from the signal, (ii) a location of each of said at least one of said sensors relative to said body region, and (iii) a timing of said generating in said signal generated by said at least one sensor.

There is also provided, in some embodiments, a method comprising:
receiving a signal form an array of sensors attached to a wearable element, wherein each sensor is attached at specified location and wherein the wearable element is designed to be worn on a body region of a subject, and determining, by a detection module, a parameter indicative of an injury to said body region, based on said signal.

In some embodiments, the parameter indicative of the injury, is at least one of: (i) an impact event associated with said subject calculated from the signal, (ii) a location of each of said at least one of said sensors relative to said body region, and (iii) a timing of said generating in said signal generated by said at least one sensor.

In some embodiments, the method may further include receiving, with respect to said subject, clinical information comprising at least some of: age, sex, temperature, heart rate, blood pressure, and blood oxidation. In some embodiments, the determining is based, at least in part, on said clinical information. In some embodiments, the parameter indicative of said injury comprises a value associated with a severity of the injury.

There is further provided, in an embodiment, a computer program product comprising a non-transitory computer-readable storage medium having program instructions embodied therewith, the program instructions executable by at least one hardware processor to operate a system comprising a wearable element designed to be worn on a body region of a subject, an array of sensors arranged at specified locations, attached to the wearable element; and a detection module in communication with each of said sensors in the array and configured to determine a parameter indicative of an injury to said body region, based on at least one signal generated by at least one of said sensors. In some embodiments, the program instructions includes: receiving a signal form the array of sensors, and determining, by the detection module, the parameter indicative of an injury to said body region, based on said signal.

In some embodiments, wherein said array of sensors is integrated into said wearable element at said specified locations.

In some embodiments, the wearable element is segmented into a plurality of zones, and wherein each of said plurality of zones comprises at least one of said sensors.

In some embodiments, each of said sensors is an electrically conductive element, wherein said signal is indicative of a loss of electrical conductivity in said electrically conductive element at said specified location, and wherein said loss of conductivity is indicative of a penetration at said specified location.

In some embodiments, the electrically conductive element is one of: a conductive wire embedded in said wearable element, a conductive wire woven into said wearable element, a conductive wire sewn onto said wearable element, conductive ink printed onto said wearable element, conducive glue applied to said wearable element, a conductive sheet, and a conductive mesh.

In some embodiments, the signal is indicative of at least one of: a force intensity applied at said specified location; a pressure applied at said specified location; direction-specific acceleration of said body region; linear acceleration of said body region; rotational acceleration of said body region; a movement of said body region; and a penetration of said body region in said specified location.

In some embodiments, the parameter indicative of said injury comprises a type of said injury, and wherein the type of injury is one of: blast wave trauma, penetration trauma, and blunt force trauma.

In some embodiments, the injury type is penetration trauma, and said determining further comprises determining at least one of: a dimension of a penetrating object; a velocity of a penetrating object; and a path of a penetrating object within said body region.

In some embodiments, the detection module is configured to receive, with respect to said subject, clinical information comprising at least some of: age, sex, temperature, heart rate, blood pressure, and blood oxidation.

In some embodiments, the determining is based, at least in part, on said clinical information.

In some embodiments, the system further comprises at least one of: an automated tourniquet, and an automated drug delivery system.

In some embodiments, the detection module is configured to operate, with respect to said subject, at least one of said automated tourniquet and said automated drug delivery system, based, at least in part, on said determining.

In some embodiments, the parameter indicative of said injury comprises a value associated with a severity of the injury.

In some embodiments, the array of sensors is configured to be arranged radially around a limb of said subject, and wherein said detection module is configured to determine said parameter indicative of the injury based on a timing differential in said timing in at least two of said specified locations.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1A:
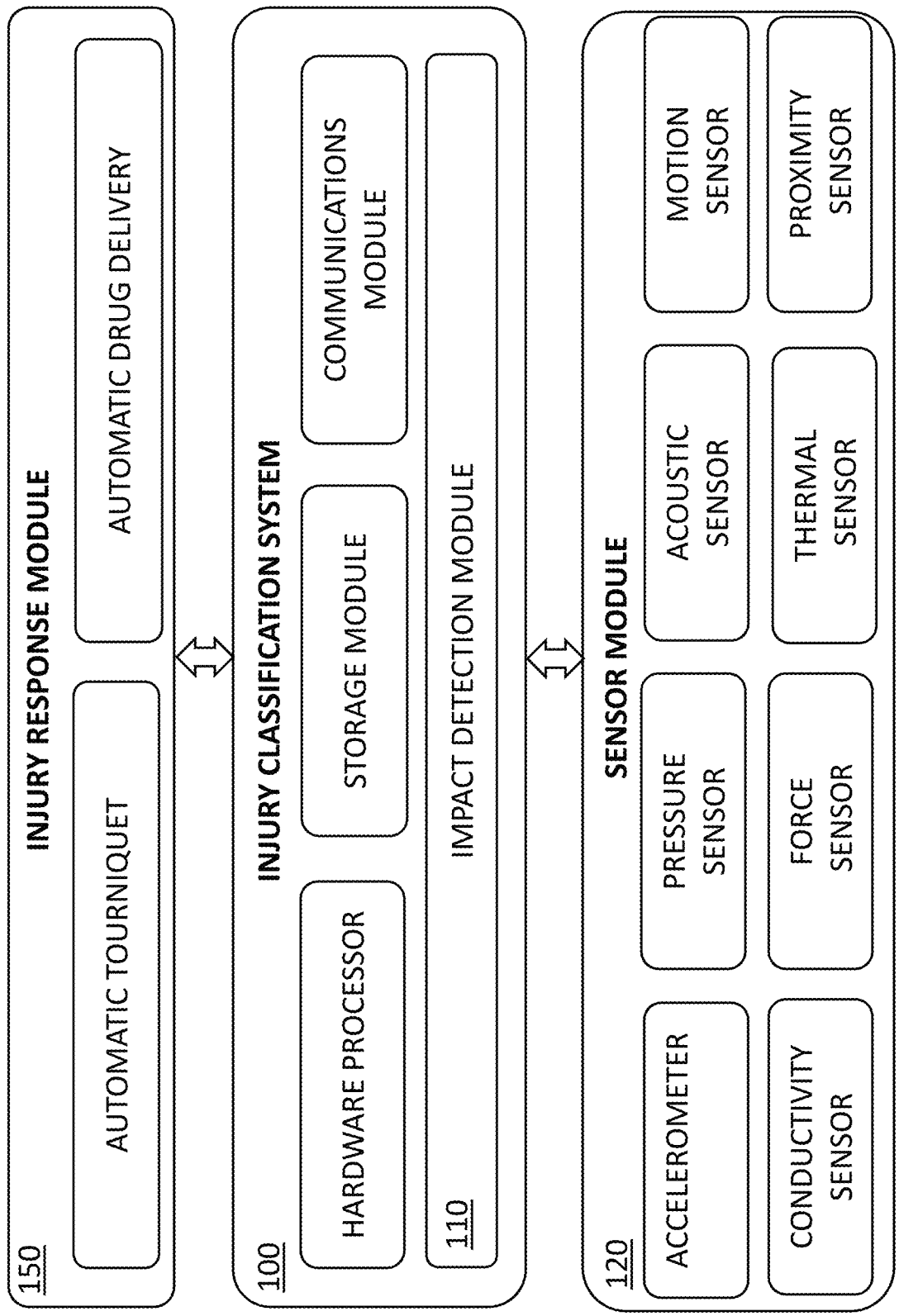
FIG. 1A is a block diagram of an exemplary injury classification system, in accordance with some embodiments of the present invention.

In accordance with some aspects of the present invention, a system, method, and computer program product are provided for automated remote monitoring, detection, and categorization and/or classification of an injury in a subject.

In some embodiments, the present disclosure comprises a wearable system incorporating means to detect when a human body is impacted by a potentially injurious impact. In some embodiments, an impact may be the result of a being hit by a projectile, shrapnel, or a significant blast wave. In some embodiments, an impact may be the result of bumping into another person or object, receiving a punch or a blow, being pushed, and/or hitting a surface (e.g., the ground, a wall) or an object (e.g., a post). In some embodiments, an impact may be sustained as a result of being hit or struck by an obstacle or other object, e.g., a moving object, falling debris, a moving vehicle, and/or any other high-velocity moving object. In some embodiments, an impact may further be the result of slipping or falling and/or exercising an unconventional movement of one or more body parts. In some embodiments, an impact may be the result of an explosion and/or detonation. Any of these impact situations may result in some degree of injury or trauma to a body part of the person.

In some embodiments, an environment in which such impact trauma may be sustained may include military training and/or combat; law enforcement training and/or operational activities; first responders training and/or operational activities; workplace environments such as construction sites or mining facilities; and/or occupations and/or operations involving the use of heavy equipment and/or potentially volatile and/or explosive materials, such as chemical plants, refineries, and/or mining facilities.

In some embodiments, the present disclosure provides for detecting, measuring and recording a type and magnitude of a force imposed by an impact to a region of the body. In some embodiments, detecting and measuring a type and force of one or more impacts to a region of the body may comprise at least one of: a magnitude of a force applied to a body part as a result of each impact, whether each impact is penetrating or non-penetrating, a location of each impact, an area affected by each applied impact force, and a timing of each impact.

In some embodiments, the present disclosure further provides for detecting, measuring and recording body kinematics and/or changes thereto preceding, associated with, or resulting from, an impact to a body part, including, but not limited to, any change in motion such as an acceleration (i.e., a change in velocity), a change in orientation, a vibration shock, and a falling process.

In some embodiments, the present disclosure provides for detecting, measuring and recording a type and magnitude of multiple forces applied to a body associated with one or more impacts, wherein detecting and measuring a type of multiple forces may comprise at least one of a magnitude of each force, whether each impact in penetrating or non-penetrating, a location of each impact, an area affected by each applied impact force, and a relative timing of each impact.

In some embodiments, data detected, measured and recorded with respect to a type and magnitude of forces imposed by one or more impacts, as well as with respect to body kinematics and/or changes thereto preceding, associated with, or resulting from, such one or more impacts, may be processed and analyzed to determine one or more parameters associated with an injury to the body, e.g., injury type, injury location, injury severity, and/or affected body regions, parts, and/or organs.

Accordingly, some aspects of the present invention provide for detection and determination of one or more parameters associated with an injury suffered by a subject. Typically, aspects of the present invention allow medics to track and treat an injured subject quickly and accurately and ensure that injured subjects who are most in need of treatment are attended to first.

In some embodiments, aspects of the present invention can be used to categorize the type and/or severity of an injury, and sort injured subjects based on medical needs, e.g., for transport and/or immediate medical treatment. Accordingly, aspects of the present invention are particularly useful under difficult conditions, such as during combat where immediate medical care is limited, time and access are critical, and injured subjects are prone to inaccurately relating their precise medical condition. Thus, some aspects of the present invention provide for improving time and quality factors in providing care to the injured under emergent conditions, as well as ensuring that the appropriate treatment is administered, and thereby potentially saving lives.

For example, in a combat environment, soldiers may be spread over a large battle zone and possibly out of direct contact with medical personnel. The present system may provide for remote triage. Impact detection could also prove valuable to police units, firefighters and other personnel working in hazardous environments. The present system may be integrated into uniforms, body armor, battle fatigue, or other garments/articles worn by an individual.

In a non-limiting example, in some embodiments, an injury including damage to a main blood vessel is detected. Unless controlled, damage to main blood vessels leads to increased chances of mortality and morbidity within minutes. The deep brachial artery and femoral artery in limbs of a human subject are examples of such main blood vessels. In some cases, life threatening injuries with regard to limbs are caused by either penetrating trauma to the limb or severing of the limb. Both severing and penetrating trauma can be caused by explosives and firearms. In cases of penetrating trauma, an object, e.g., shrapnel, typically cuts through the limb and rips the blood vessel in its path in the body (internal ballistics). In cases of amputation trauma, the entire limb is severed, leaving blood vessels cut and exposed. Both types of injury (i.e., penetrating trauma and amputation), involve damage to skin of the subject. In cases of penetrating trauma, the projectile pierces the skin and enters the limb, and in cases of amputation the skin is ripped away together with the limb. Thus, a correlation exists between damage to internal portions of the limb (tissue and blood vessels underlying the skin) and damage to skin covering the limbs. Accordingly, some aspects of the present invention provide a system comprising one or more sensors for placement on/or in close proximity to skin of the subject using the system, to detect an injury, e.g., penetration or amputation, to a limb or other body portion.

In some aspects, detection of the injury includes identifying that an injury occurred, and determining at least one parameter indicative of the injury (e.g., a parameter indicative of a type of the injury and/or a severity of the injury). The system typically comprises a wearable system having the sensors coupled thereto, the wearable system being shaped and sized to cover a body part of a user such that the sensors are placed in a predetermined arrangement over the relevant body part.

In some aspects, the wearable system comprises wearable element in the form of a garment having the sensors integrated into the wearable element, e.g., into a wicking fabric. When the wearable system is worn by a user in accordance with some aspects of the present invention, the integrated sensors from an array of sensors in a predetermined arrangement over the relevant body part, such that a strong correlation exists between a force applied to and/or damage caused to the wearable element of the wearable system and an injury to a body region of the user, e.g., a limb of the user. By sensing and quantifying force sensed and/or damage sustained by the wearable system, it is possible, in accordance with some aspects of the present invention, to assess force applied and/or damage sustained by body parts and organs of the user. In particular, it is possible to assess damage to limbs of the user (including tissue, bones, and blood vessels in the limb), since limbs are generally cylindrical organs and the locations of the blood vessels in the limbs are well defined with respect to the limb itself (generally, the main blood vessels follow the bone structure which is concentric to the limb (arm or leg). Thus, when snuggly fit around a limb of a user, the wearable system is configured to detect a type and severity of an injury to the limb.

In some aspects, the one or more sensors of the wearable system are arranged in an array of sensors which is disposed with respect to a specified location in a body region of the user when the system is worn by the user. In some aspects the one or more sensors include electrical conductivity sensors, and/or pressure sensors, and/or force sensors and/or accelerometers. In response to impact to the sensors in case of an injury to the user, the wearable system is configured to identify a parameter of the injury (e.g., a type and/or a severity of the injury). For example, the one or more sensors measure force intensity or magnitude of the impact at the specified location, and/or a pressure applied at the specified location. Additionally, or alternatively, the one or more sensors measure kinematics and movement of the body region and/or direction-specific, linear, and/or rotational acceleration of the body region. Further, additionally or alternatively, the system may be configured to indicate penetration trauma to the body region at the specific location through a change in the measured electrical conductivity of the sensors.

In some embodiments, each of the sensors is in communication with a detection module of the wearable system. The detection module typically comprises a processor comprising processing circuitry which is configured to receive a signal from each one of the sensors in the wearable system to detect a change in the signal in response to the impact to the sensor and calculate a parameter of the injury based the change in the signal. More specifically, the detection module determines the parameter of the injury based, at least in part on at least one of, the change in the signal generated by sensor in response to the impact, a location of the impacted sensor relative to the body region, and a timing of the detected change in the signal. Additionally, or alternatively, the detection module is configured to a predicted force on the body region due to the impact.

Figure 1B:
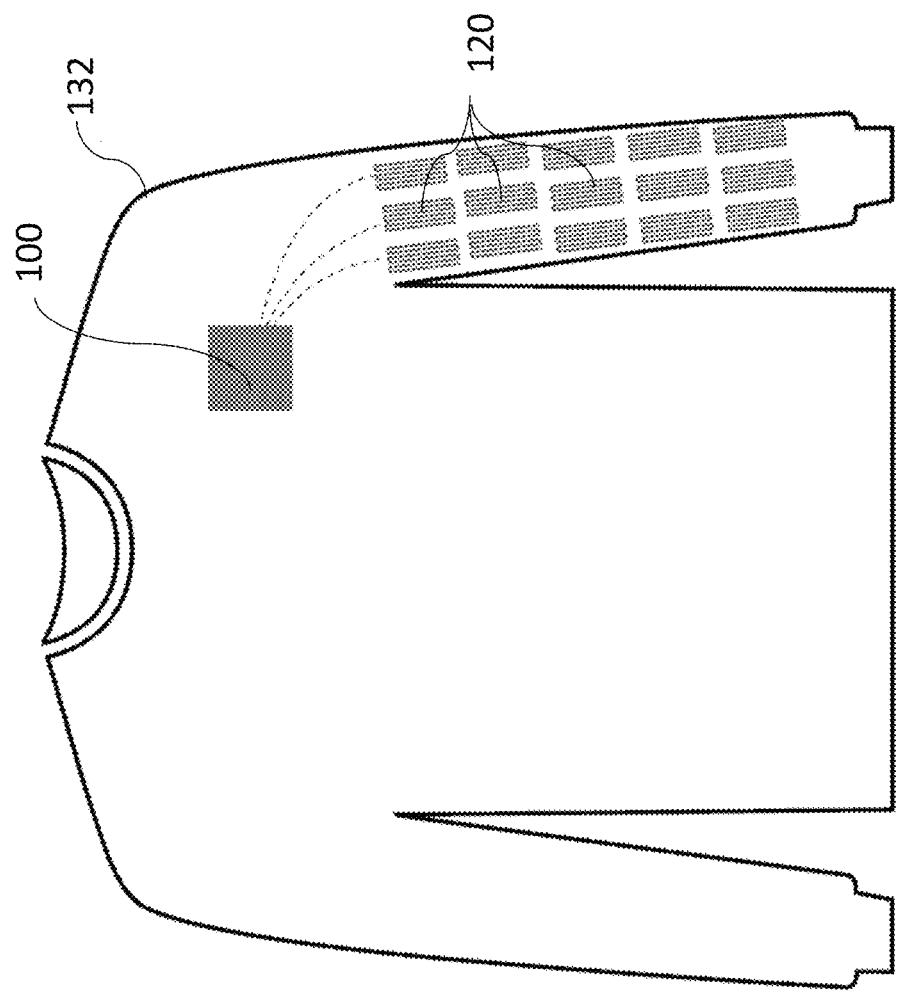
FIGS. 1B-1C are schematic illustrations of an exemplary wearable injury classification system, in accordance with some embodiments of the present invention.
Figure 1C:
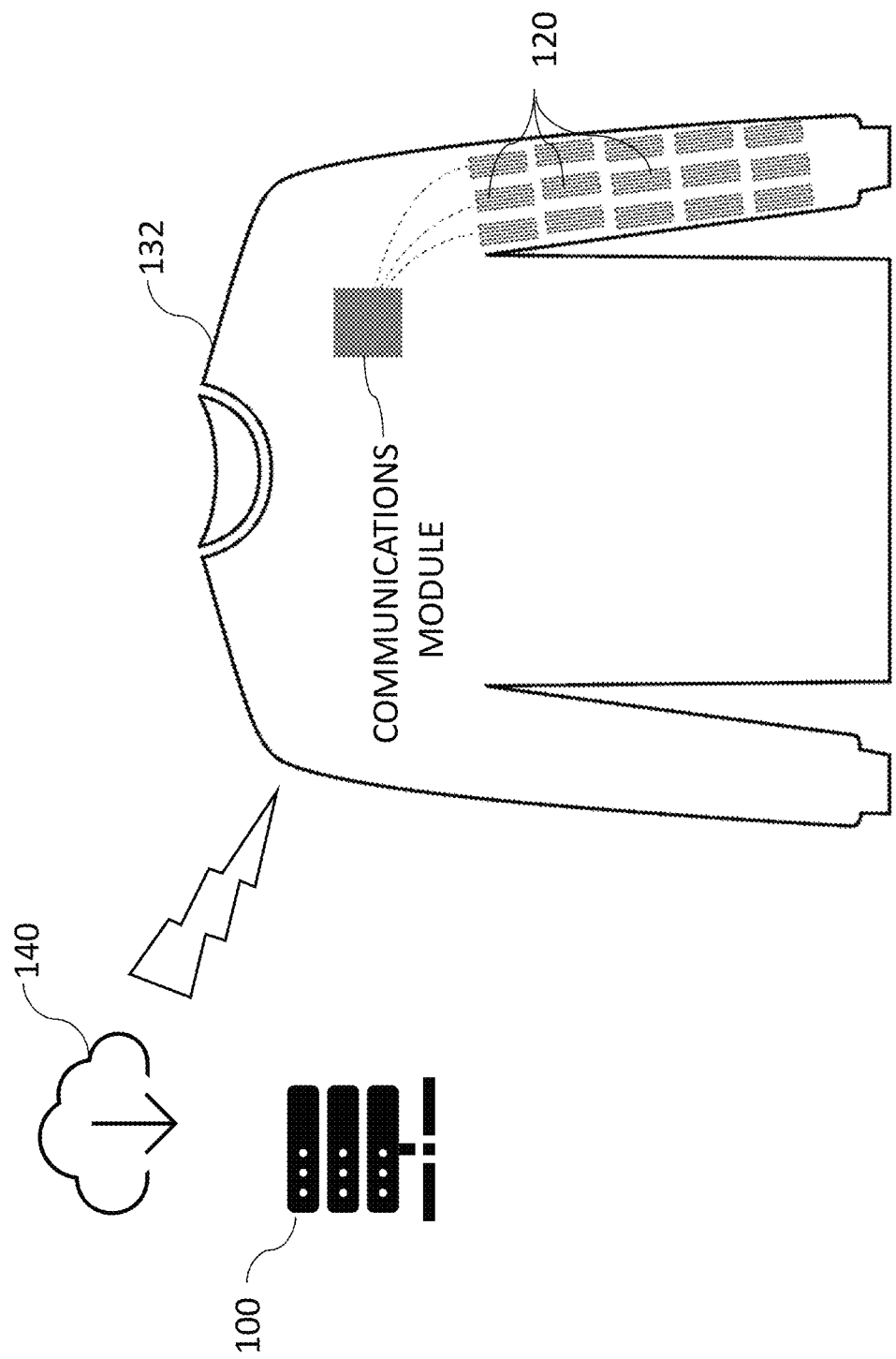

Reference is first made to FIG. 1A which is a block diagram of an exemplary injury classification system 100, and FIGS. 1B-1C which are schematic illustrations of exemplary wearable injury classification systems 100, in accordance with some embodiments of the present application.

System 100 may include one or more hardware processor(s) and one or more non-transitory computer-readable storage module(s). The storage module(s) may have stored thereon program instructions and/or components configured to operate the hardware processor. The program instructions may include one or more software modules. The software components may include an operating system having various software components and/or drivers for controlling and managing general system tasks (e.g., memory management, storage module control, power management, etc.), and facilitating communication between various hardware and software components.

System 100 may comprise an impact detection module 110 and a sensor module 120. The instructions for operating impact detection module 110 and sensor module 120 may be loaded from the storage module to be executed by the processor(s). Impact detection module 110 may communicate with sensor module 120 and/or any external resource and/or destination via a plurality of communication modalities, e.g., wire-based, wireless, RF, cellular, etc. in some embodiments, system 100 may include one or more additional modules and/or components, such as a power source (e.g., a battery pack, a solar panel, etc.).

Impact detection module 110 may provide for calculating, sensing, monitoring and recording impact events on an impact surface, based on data/signal received from, e.g., sensor module 120. The sensors of sensor module 120 may be incorporated into the impact surface. The sensors can be integral with, attached to, or located behind various types of impact surface including various types of garments that can be worn by an individual. As used herein, an impact event is an event sensed by at least one sensor in sensor module 120 as a result of ballistic or non-ballistic impacts on an impact surface.

In some embodiments, system 100 is an injury classification system communicatively connected to sensor module 120 and used to detect ballistic or non-ballistic type impacts on an impact surface. System 100 processes the impact data detected by the sensor module 120 and stores the data for analysis at a later time or outputs the data to a third party system for review and/or analysis.

System 100 as described herein is only an exemplary embodiment of the present invention, and in practice may be implemented in hardware only, software only, or a combination of both hardware and software. System 100 may have more or fewer components and modules than shown, may combine two or more of the components, or may have a different configuration or arrangement of the components. System 100 may include any additional component enabling it to function, such as a motherboard, data busses, power supply, a network interface card, a display, an input device (e.g., keyboard, pointing device, touch-sensitive display), etc. (not shown).

As seen in FIG. 1C, in some embodiments, one or more component of system 100 may be co-located or distributed, or the system could run as one or more cloud computing instances, containers, and/or virtual machines, as known in the art.

As shown in FIGS. 1B-1C, system 100 may be integrated with/include an article of clothing, a garment, and/or any flexible substrate or wearable element, such as a wearable element 132 designed to be worn on a body region of a subject, which is able to conform to a surface of the subject's body region so as to facilitate comfortable and safe intimate proximity of the system to the body. For example, wearable element 132 covers a top region of the body including arms of the user.

In some embodiments, wearable element 132 comprises one or more layers or substrates configured to cover a body region wholly or partially, wherein sensor module 120 is integrated into wearable element 132 at said specified locations. It is noted that wearable element 132 may additionally or alternatively be shaped and sized to cover other body regions of the user, e.g., whole or portions of the subject's torso, one or more limbs, hands, feet, head, face, etc. In some embodiments, wearable element 132 may have a relatively comfortable and/or relaxed fit relative to the body region. In other embodiments, wearable element 132 may have a close, tight and/or compression fit over skin of the user such that sensor module 120, which are typically integrated into wearable element 132 at specified locations, are brought into close proximity with skin of the user at the specified locations.

In accordance with some embodiments of the present invention, wearable system 100 comprises a sensor module 120 comprising one or more sensors arranged in a predetermined pattern over wearable element 132 or portions thereof. For example, in some embodiments, wearable element 132 may be segmented into a plurality of zones and/or sectors, and each of the plurality of zones or sectors may comprise at least one sensor associated with the zone or sector. In some embodiments, the zones or sectors off wearable element 132 may be distributed over the whole or one or more portions of wearable element 132, and may be of equal or varying sizes. In some embodiments, sensors of sensors module 120 may be arranged in a grid pattern which corresponds to the zones or sectors of wearable element 132. In some embodiments, each sensor in sensor module 120 is associated with a specified location over wearable element 132, e.g., a specified one of the zones or sectors.

In some embodiments, sensor module 120 may comprise a set of sensors comprising one or more of each of a plurality of types of sensors. In some embodiments, each zone or sector in wearable element 132 may comprise one or more sensors of one or more types. For example, sensor module 120 may comprise a plurality of electrical conductivity sensors associated with at least some of the zones or sectors of wearable element 132. In some embodiments, with respect to certain types of sensors, such as pressure sensors and/or accelerometer, sensor module 120 may only comprise one a single unit located at a specified area of wearable element 132.

In some embodiments, sensor module 120 may comprise a plurality of sensors of a plurality of types, including, e.g., one or more of each of an accelerometer; a pressure sensor (shock wave sensor); a force, strain and/or stress sensor; a thermal sensor; an acoustic sensor; a motion sensor; a proximity sensor; and/or an electrical conductivity sensor.

In some embodiments, other and/or additional sensors may comprise, e.g., a skin surface temperature sensor; a skin conductance sensor; a respiration sensor; an oxygen saturation sensor; an electrocardiograph (ECG) sensor; a heart rate sensor; an electroencephalograph (EEG) sensor; a joint bend sensor; and/or a muscle activity sensor.

In some embodiments, the sensors of sensor module 120 may be arranged such that each zone or sector of wearable element 132 has one or more sensors. In some embodiments, each zone or sector comprises a set of sensors comprising one each of several types of sensors, e.g., a force sensor, an accelerometer, and an electrical conductivity sensors. In some embodiments, each zone or sector of wearable element 132 may comprise the same or a similar set of sensors. In some embodiments, each zone or sector may comprise a specific set of sensors comprising one or more sensors of varying types.

In some embodiments, sensor module 120 is typically in communication with impact detection module 110 of system 100, such that impact detection module 110 receives signals from sensor module 120 and detects changes in the signals generated by sensor module 120 to determine an injury sustained by the user.

In some embodiments, each sensor for sensor module 120 may be configured to measure one or more parameters associated with an impact to a region for the body. For example, sensors of sensor module 120 may be configured to measure and monitor at least one of a magnitude or intensity of a force of an impact at a specified location, over a specified area of the body, or over the entire body; a pressure applied at the specified location, over a specified area of the body, or over the entire body; a penetration or penetration-related trauma to the body at one or more specified locations; and/or direction-specific acceleration and/or movement of an impacted body region, another body region, or the whole body.

In some embodiments, a force sensor of sensor module 120 as may be incorporated into system 100 may be formed from any structures that produce an output signal that is responsive to applied force. In a typical scenario, the amount of output signal that is produced by a force sensor will be linearly or non-linearly proportional to the amount of applied force. A force sensor may include a piezo-electric film or another type of piezoelectric sensors, e.g., in the form of a wire or a fiber, which can quantitatively measure the impact over an area surface. Piezoelectricity is typically the electric charge that accumulates in certain solid materials in response to applied mechanical stress. Piezoelectric materials are available in thin films with elastic properties.

Piezoelectric sensing material may be integrated into wearable system 100 by gluing, e.g., in a pocket, or between fabric layers. Piezoelectric material generally allows for passive monitoring and does not require power to operate. The piezo element produces electric current in response to pressure. This can be used as a "wake up" module for the when the system is in deep sleep mode until a signal is received from the piezoelectric sensor, thereby allowing power conservation in wearable system 100. In this configuration the shockwave energy is used to "wake up" the system and trigger the injury detection and classification process. Accordingly, the piezo electric film sensor generates an electrical charge across conducting materials when subjected to an impact, and the amount of charge generated is directly proportional to the impact magnitude. In some embodiments, piezo-film sensors may be configured to pick up vibrations, to detect frequencies associated with a ballistic impact, the location of ballistic impacts on the body, and/or blast overpressure.

In some embodiments, a force and/or pressure sensing functionality may be implemented into wearable system 100 using, e.g., a pressure sensor integrated circuit (IC), with analog or digital output, which may be used as a standalone component integrated in one or more locations into wearable element 132. Additionally, or alternatively, a pressure sensor may be integrated directly into a main board of impact detection module 110.

In some embodiments, a force-sensing resistor (FSR) may be used, which is a component whose resistance changes when a force, a pressure, or a mechanical stress applied thereto. An example of an FSR configured for use in accordance with some embodiments of the present invention is a Pressure-Sensitive Conductive Sheet (e.g., Velostat material). An FSR may be sufficiently flexible to allow integration thereof into a substrate layer, such as wearable element 132. The FSR can be integrated into wearable element 132 using glue, sewing, and/or in a patch or packet or any other common procedure in fabrication of wearable element 132. An FSR is typically in communication with impact detection module 110 which monitors the FSR changes in properties of the FSR. The FSR readings are calibrated to detect a pressure level typical to the shockwave of an explosive blast. FSRs typically respond rapidly to pressure changes but have a relatively slow return to a normal state, allowing improved detection by impact detection module 110. This property of the FSR is generally advantageous for low-power systems, as it generally reduces the duty cycle and prolongs battery use.

In some embodiments, any force and/or pressure sensing sensor or elements of the present disclosure, e.g., piezoelectric, FSR, and/or any other type may be integrated into wearable element 132, which may be a fabric layer, using any suitable means. For example, in some embodiments, such elements may be printed onto wearable element 132, sewn onto wearable element 132, embedded in wearable element 132, woven into wearable element 132, and/or glued to wearable element 132.

In some embodiments, an accelerometer of sensor module 120 as may be incorporated into system 100 is an exemplary sensing device that is configured to sense a change in motion. In some embodiments, impacts involving high-velocity projectiles hitting a body may result in the kinetic energy of the projectile being absorbed by the target. Certain types of projectiles, such as high-damage gun bullets and high velocity high mass rounds used in assault rifles and machine guns, have high amounts of kinetic energy. This energy transformation is detectable by acceleration sensing, as a portion of the kinetic energy of the projectile is absorbed by the body in a very short time (i.e., a spike). Thus, in some embodiments, wearable system 100 performs acceleration sensing.

Generally speaking, a change in motion may refer to one or more of an acceleration (i.e., a change in velocity), a change in orientation, a vibration shock, and a falling process. Conventional accelerometers are capable of sensing various changes in motion along one or more axes. An accelerometer typically provides an output signal representative of a "g-force" acting on an object that is free to move (i.e., the "g-force" is the object's acceleration relative to free-fall due to the vector sum of non-gravitational forces acting on the object). A g-force (denoted by the unit g) causes stresses and strains on an object, and hence large g-forces may be destructive. Accelerometers may include piezoelectric or capacitive components to convert mechanical motion into an electrical signal. Piezoelectric accelerometers rely on piezoceramic materials or single crystals, whereas capacitive accelerometers typically employ a silicon micro-machined sensing element (a micro-electrical-mechanical system, or MEMS, sensing element). In some embodiments, acceleration can be measured in procedures that are similar to pressure sensing described herein. For example, a dedicated sensor IC (e.g., a MEMS accelerometer) and/or either using FSR or a piezo element. Both FSR and piezo are generally highly sensitive to deflection, which in turn is correlated with acceleration of a wearer's body part.

In some embodiments, acoustic or sound sensors of sensor module 120 as may be incorporated into system 100 may be configured for registering high-energy acoustic signatures produced by ballistic impacts.

In some embodiments, electrical conductivity sensors of sensor module 120 may comprise elements configured to provide an indication with respect to a loss of electrical conductivity at a specified location, and wherein said loss of conductivity is indicative of a penetration trauma at said specified location. In some embodiments, electrical conductivity sensors of the present disclosure may be configured to provide an indication of a degree of loss of conductivity and/or a complete loss of conductivity at a specified location of wearable element 132. For example, an electrical conductivity sensor may be one of a conductive wire embedded in wearable element 132, a conductive wire woven into wearable element 132, a conductive wire sewn onto wearable element 132, conductive ink printed onto wearable element 132, conducive glue applied to wearable element 132, a conductive sheet comprising wearable element 132, and/or a conductive mesh comprising wearable element 132.

Figure 2A:
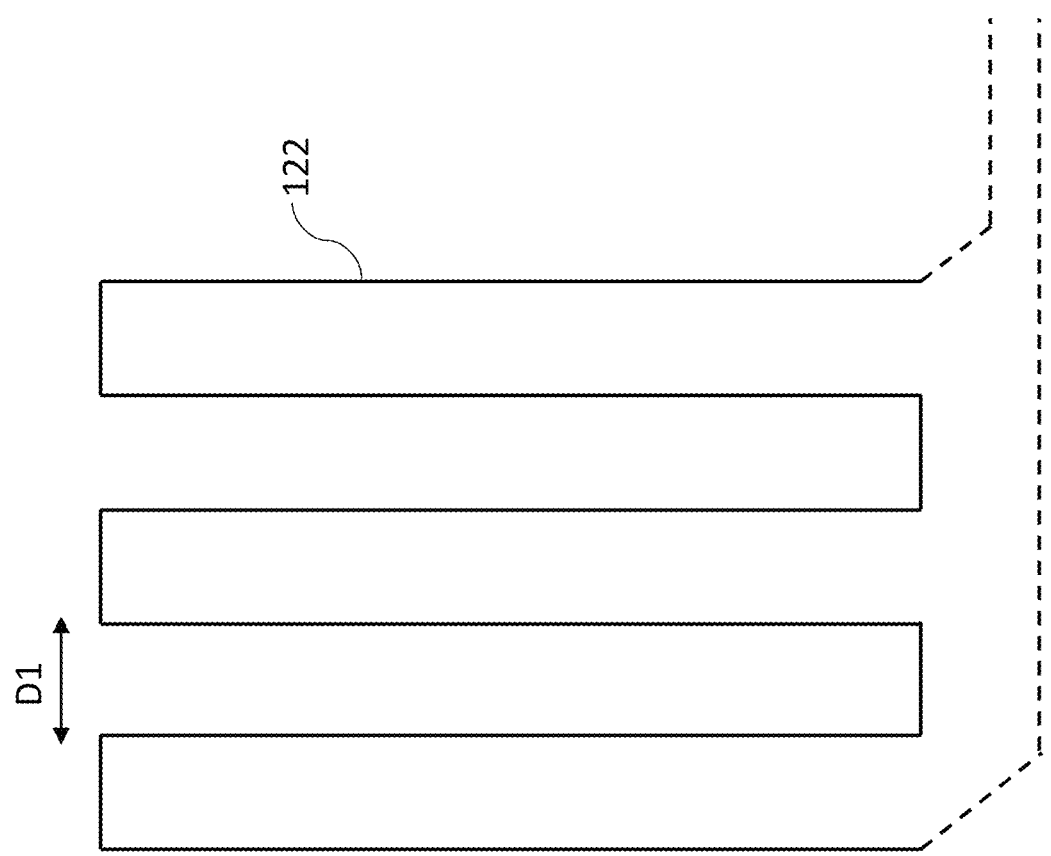
FIGS. 2A-2B illustrate examples of an electrical conductivity sensor as may be integrated into an exemplary injury classification system, in accordance with some embodiments of the present invention.
Figure 2B:
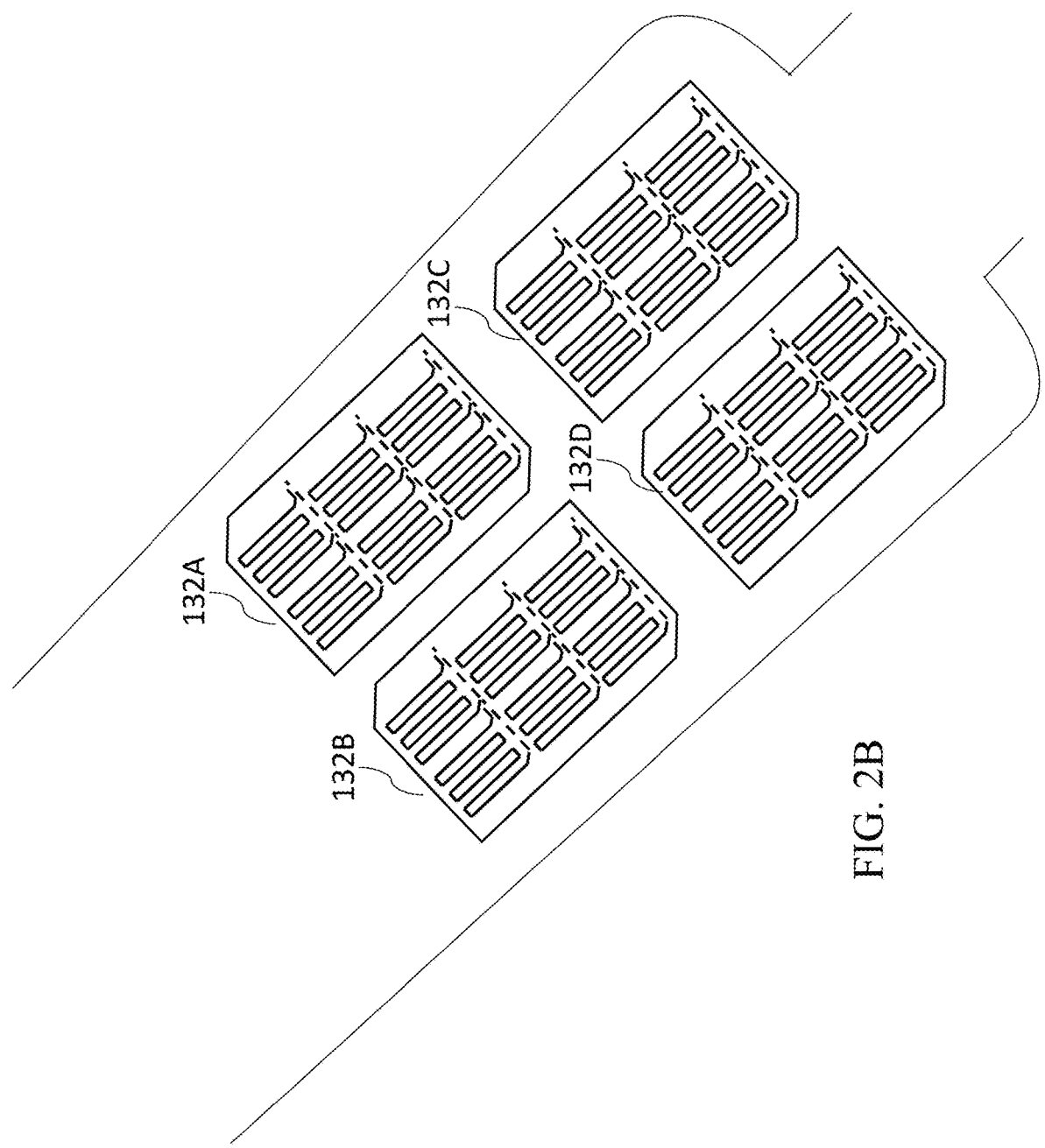

FIGS. 2A-2B illustrate examples of an electrical conductivity sensor as may be integrated into sensor module 120. In some embodiments, sensor module 120 comprises at least one electrically conductive sensor element 122. Typically, sensor 122 comprises an electrically conductive wire integrated into wearable element 132. For some embodiments, wearable element 132 is segmented into a plurality of zones, e.g., sensor zones 132A-D in FIG. 2B, each zone 132A-D comprising at least one sensor 122 (i.e., at least one electrically conductive sensor 122). A plurality of sensor zones 132A-D may form an array of sensors 122. Each sensor 122 is in communication with impact detection module 110 such that a change in the signal generated by sensor 122, e.g., a change in electrical conductivity of sensor 122, is detected by impact detection module 110. A change in the electrical conductivity of sensor 122 may be a reduced conductivity or a complete loss of electrical conductivity. The reduction or loss in electrical conductivity of sensor 122 typically occurs as a result of damage to wearable element 132 which causes damage to sensor 122 (e.g., tearing of the conductive wire in case of penetration or a blast wave). The reduction or loss in electrical conductivity in sensor 122 is indicative of penetration or amputation of the body region which is covered by wearable element 132. Multiple sensor zones 132A-D are shown in FIG. 2B covering one arm by way of illustration and not limitation. It is noted that wearable element 132 may comprise any number of sensor zones 132A-D which are integrated into wearable element 132 in any suitable location. Typically, sensor zones 132A-D may form a covering wearable element enveloping a body region of the subject (e.g., as a sleeve around a limb of the user when wearable system 100 is worn by the user). Generally, arranging multiple zones of electrically conductive sensor 122 around a body region, e.g., a limb, of the user facilitates obtaining increased information as to the parameter of the injury sustained by the user.

In some embodiments, a number of sectors or sensor zones 132A-D may be determined by a desired locational detection resolution and/or accuracy. For example, increasing the number of sensor zones 132A-D (and thus the number of sensors 122) provides for greater locational detection resolution accuracy, wherein an impact location may be pinpointed to within a smaller area. In some embodiments, enveloping or surrounding a region, e.g., a limb, with sensors radially or at last partially radially may provide for detection of a full perforating penetration of the limb (e.g., side to side or entry and exit points of a projectile). Additionally, or alternatively, multiple radially arranged sensor zones 132A-D facilitate determining a radial location of the penetration. Further additionally or alternatively, multiple radially arranged sensor zones 132A-D facilitate determining full amputation of the limb.

FIG. 2A is a schematic illustration of a single zone 132A-D comprising a single electrically conductive element sensor 122. As described hereinabove with reference to FIG. 1B, wearable element 132 comprises a sensing fabric layer by having electrically conductive sensor 122 (e.g., a conductive thread/wire) integrated into wearable element 132. An injury caused by a projectile (a penetrating object) or blast wave typically damages sensor 122, thereby interrupting a structure of the sensor by physically breaking or cutting the sensor, and/or by removing a portion of wearable element 132. The resulting impact to the sensor is sensed by impact detection module 110 through current loss (disconnection) or conductivity change (material loss). FIG. 2A shows a possible configuration of electrically conductive sensor 122, by way of illustration and not limitation. It is noted that other configurations of sensor 122 are included in the scope of the present invention.

In some embodiments, sensor 122 and zone 132A-D have three main dimension parameters determined based on, e.g., a desired resolution and/or accuracy level of system 100, sensor dimensions, technical limitations associated with the sensors and/or wearable element 132, and/or other similar considerations. In some embodiments, a length of the zone and a width of the zone may be determined in accordance with these considerations. Generally, these dimension parameters contribute to detection of the injury by wearable system 100.

More specifically, in some embodiments, each sensor 122 comprises a plurality of conductive wires arranged such that a distance D1 between portions of the conductive wire determines a detection accuracy of sensor 122. In cases in which a single sensor 122 comprises multiple conductive wires of varying sizes that are arranged in a single zone 132A-D, distance D1 exists between the multiple conductive wires in a manner similar to that shown in FIG. 2A. Typically, a relatively smaller distance D1 between portions of the conductive wire of sensor 122 contributes to increased sensing and resolution, allowing determining of a size and/or a shape of a penetrating object.

In some embodiments, each zone 132A-D has a width. Generally, a relatively small width W1 allows for an increased number of sensor zones 132A-D radially. Multiple sensor zones 132A-D arranged radially generally allow for improved obtaining of information regarding of a penetrating point and the exit point of the projectile (if exists), thereby contributing to determining the trajectory of the penetrating object through the body portion.

Reference is still made to FIGS. 1A-B. In accordance with some embodiments of the present application, impact detection module 110 detects the change in the signal generated by the sensors in wearable system 100 in response to impact to the sensors, as described hereinabove. Generally, based on the detected change, a location of the impacted sensor and a timing of the change in the signal, determination of the parameter of the injury is determined by impact detection module 110.

Reference is now made to FIG. 2B, which is a schematic illustration demonstrating use of wearable system 100, in accordance with some embodiments of the present invention. For example, a portion of wearable element 132 which forms a sleeve of wearable system 100 comprises multiple sensor zones 132A-D disposed abut a body region, e.g., surrounding a limb of the user.

Figure 3:
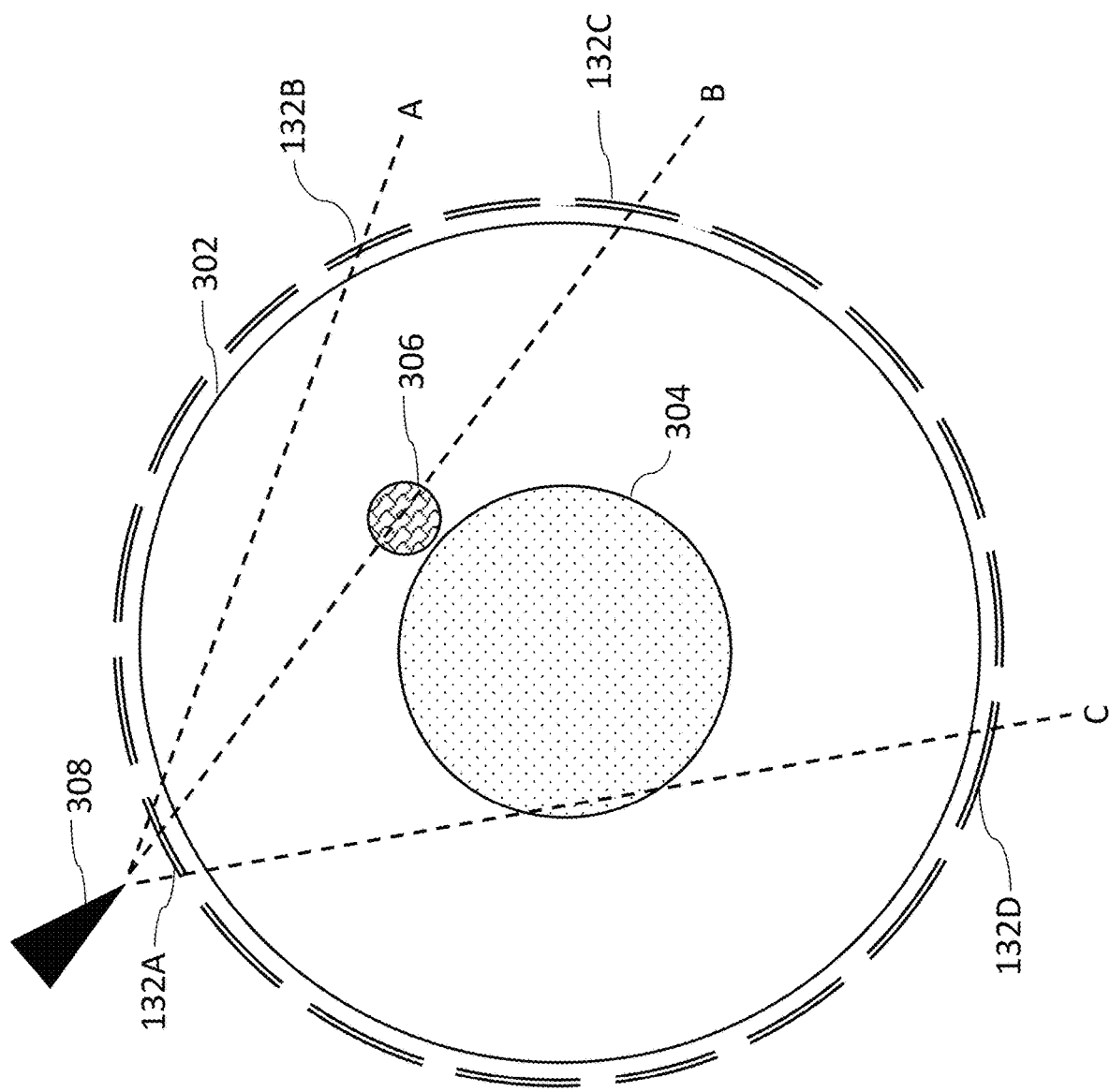
FIG. 3 is a schematic illustration demonstrating the calculation for limb injury detection and classification in accordance with some embodiments of the present invention.

With reference to FIG. 3, limb 302 bone 304 and main blood vessel or artery 306 that are centrally located within limb 302. Limb 302 is covered by a wearable element 132 comprising a plurality of sensor sectors or zones, e.g., sensor zones 132A-E. Each one of sensor zones 132A-E is part of a wearable element 132 worn over limb 302. sensor zones 132A-E comprise sensors 122 as part of sensor module 120, e.g., electrically conductive sensors 122, wherein each sensor 122 is in communication with impact detection module 110 (not shown for clarity). Typically, the zones or sectors of wearable element 132 are disposed about a circumferential surface of limb 302. In other embodiments, wearable element 132 may cover other and/or additional body regions. When in use, impact detection module 110 continuously or periodically monitors the electrical signals generated by sensors 122, thereby verifying integrity of the sensors by validating that current is running through the sensor. In an event in which current loss is detected in a given sector, the event with a time stamp is recorded by the detection module. Loss of the signal (either reduction or complete loss) forms the basis for injury detection and classification by wearable system 100. Analysis is typically based on the following:

Location and number of zones which measure and/or a register a parameter associated with an impact to the wearer, e.g., a loss in electrical conductivity as a result of an impact to the wearer;
intensity and/or magnitude of the parameter measured by each sensor in connection with the impact, e.g., partial or complete loss of electrical conductivity; and
relative timing of the measurement from each sensor.

In some embodiments, an impact may register sensor reactions of various types in various locations about wearable element 132. For example, one or more sensors may indicate measurements associated with penetrating trauma, blunt force trauma, blast wave trauma, and/or any other type of trauma and/or force being operated on the body region.

In some embodiments, each sector or zone comprising one or more types of sensors may measure and/or register one or more reactions in connection with an impact to the body region, such as, but not limited to:
One or more parameters associated with a force or pressure applied to a sector or zone, including:
magnitude or intensity of the force or pressure,
an extent of an area to which the force or pressure is applied,
a direction of the application of force or pressure;
one or more parameters associated with a penetration within a sector or zone:
location of entry and exit points,
size and shape of entry and exit points,
angle of entry and exit,
one or more parameters associated with any change in motion of the body region:
acceleration (i.e., a change in velocity),
a change in orientation,
a vibration shock,
a falling process.
one or more physiological parameters associated with the wearer, including:
body temperature sensor,
skin conductance,
respiratory rate,
blood oxygen saturation,
electrocardiograph (ECG),
heart rate,
electroencephalograph (EEG) signal, and/or
muscle activity.
one or more parameters associated with post-impact movement of a wearer, which may be indicative of injury type and/or severity, including:
wearer mobility,
wearer posture (e.g., upright or reposed),
head, limb, and/or other body part movements.

Additionally, or alternatively, detection module is configured to receive, physiological and clinical information regarding the user, for example, age, sex, temperature, heart rate, blood pressure, and/or blood oxidation. For some embodiments, impact detection module 110 is configured to determine the parameter of the injury to the user based at least in part on the physiological and clinical information.

In some embodiments, a location of each zone for which a loss in the signal is detected. For example, a projectile 308 may hit limb 302 at a specified location within zone 132A. Projectile 308 may travel within limb 302 in various paths, e.g., path A indicates an exit wound within zone 132B, which avoids artery 206 and may be indicative of a more superficial wound which is unlikely to result in considerable damage to major blood vessels in the limb. Path B exits at zone 132C which may indicate damage to artery 306. Path C exits within zone 132D, which may indicate at least some damage to bone 304.

A timing of each measurement within each zone may be indicative of the sequence of impacts affecting the wearer. For example, when an impact to zone 132A precedes impacts to sensor zones 132B, 132C, or 132D, it may be deduced that the impact to zone 132A is an entry wound, whereas the impacts to sensor zones 132B, 132C, or 132D are exit wounds.

In some embodiments, a simultaneous measurement from multiple adjacent zones may indicate penetration of a lager object compared to loss of only a single zone, hereby potentially indicating a more severe injury. In general, a larger penetrating object results in increased severity of the injury. This analytical process can be combined with a numerical model of the limb and the blood vessels in the limb.

The analysis generally compares the damage to the structure of sensor zones 132A-E to the known structure of the limb to determine the probability of damage to the main blood vessel in the limb as a result of a penetrating object or amputation of the limb. Furthermore, in some embodiments, a structure of sensor zones 132A-E enables further analysis based on the ability to determine the shape of the entry and/or exit holes of the penetrating object. Different projectiles vary in diameter and internal ballistic characteristics. Analysis of the size, shape and/or location of the entry and/or exit holes can classify the type of penetrating object.

Timing of the loss of a signal from a zone is typically in accordance with properties of the penetrating object (speed, kinetic energy). Thus, a time gap that is greater than a specified threshold is generally associated with either separate penetration events or a low energy penetrating object. For example, the type and severity of the injury are determined based on a timing differential in the loss of the signal between a zone in a first radial location and a zone in a second radial location.

Figure 4:
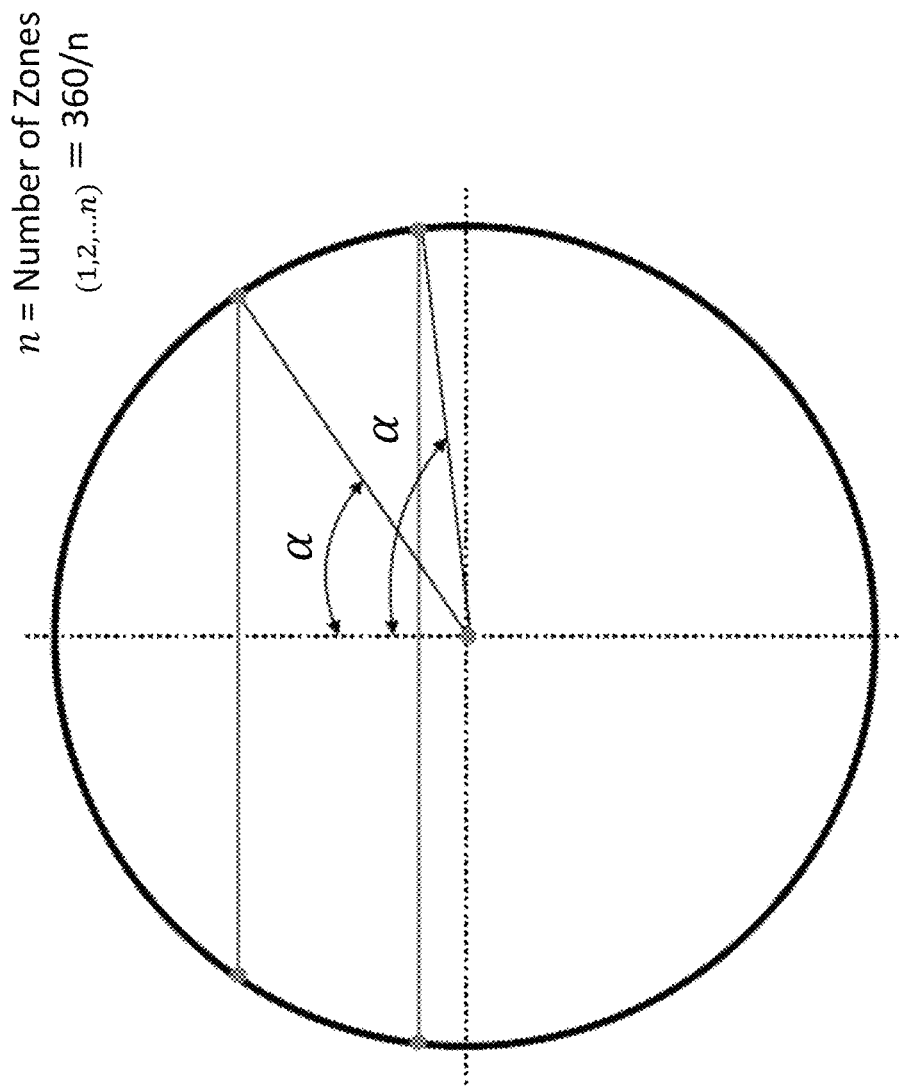
FIG. 4 is a schematic illustration demonstrating the calculation for limb injury detection and classification, in accordance with some embodiments of the present invention.

Reference is now made to FIG. 4, which is a schematic illustration demonstrating the calculation for limb injury detection and classification in accordance with some embodiments of the present invention. Wearable system 100 comprises N number of sensor zones 132A-E. As described herein, sensor zones 132A-D are in communication (e.g., electrically coupled to) impact detection module 110 which comprises a processor, e.g., a microprocessor, running embedded computer-readable program instructions software having an injury classification algorithm. The following description provides examples of detection of amputation and of penetration injuries, in accordance with some applications of the present invention.

In some embodiments, limb loss may be identified by calculating a ratio between damaged zones and intact sensor zones. The damage ratio may then be denoted as then DR=Nd/N. If DR is greater than a predetermined threshold value, a severing or amputation event may be determined. Predetermined threshold values depend on the level of confidence desired. The analysis could be time-based or time agnostic (i.e., the time of the loss of the signal from the zone).

In cases of a penetrating object piercing the limb, the object typically creates a path of damage. This path is approximated initially as straight line, and the problem may be stated as a geometrical problem of a chord in a circle, e.g., a straight line segment whose endpoints both lie on a curved perimeter of the circle. My determining impacted points on the perimeter of the impacted body region, it is possible to determine an internal path and/or trajectory and any injured internal organs. The principle mathematical procedure is the following sequence (assuming 2 damaged zones):

```
Q_critical = z (critical angle)
N = number of zones (z1,z2, ...N). Zones are arranged in equal spacing radially
Sx = damaged sector x (x is 1 – N)
Sy = damaged sector y (y is 1 – N)
Qx = (3200 * X ) / N (damaged sector x angle)
Qy = (3200 * X ) / N (damaged sector x angle)
If Qx > Qy
    Delta_Q = Qx – Qy
Else
    Delta_Q = Qy – Qx
```

```
It Delta_Q > 180
    Q_final = 3200 – Delta_Q
Else
    Q_final = Delta_Q
If Q_final >= Q_critical Main blood vessel damage is true.
```

In cases of damage to multiple zones, analysis may include finding the longest possible chord based on damaged zone pairs.

Additionally, or alternatively, damaged zones may be clustered. The clustering mechanism is based on accumulating damaged zones or sectors that are adjacent. For example, in a system comprising 12 zones, if the damaged zones are 2, 3, 6, 7, the clusters will be: cluster A: 2, 3. And Cluster B: 6, 7. Clusters typically provide information on entry and exit points created by the penetrating object, such as size and shape. In combat, some of the projectiles have specific ballistic properties. The cluster can provide information to identify the projectile type. For example, a small entry hole with big exit hole is a common situation with military ammunition.

Further features of the present system may include:
Determining a diameter and/or size and/or shape of the penetrating object in order to identify high energy projectiles (mass and speed).
Clustering based on time stamps, wherein different impacted zones may be clustered as associated with the same impact if they have the same time stamp within a predefined difference (in the micro- to millisecond range).

In some embodiments, these analyses can be based on body region models (e.g., a 3D model of a limb) based on the spatial resolution of zones within wearable element 132. Such a 3D model typically provides enhanced information regarding the shape of the entry and exit points, e.g., signature and diameter. In some embodiments, the analyses may include a lookup table of restricted paths within a body region, e.g., a limb, based on entry and/or exit angles. In this case, the lookup table includes, e.g., circle chords that may indicate damage to main blood vessel, based on measurement of entry and exit angles.

In some embodiments, these analyses are based on the fact that an article of clothing generally has a fixed orientation with respect to the human body, in particular when the clothing is a tight fit on the body. Therefore, a location of each zone or sector of wearable element 132 relative to the body region may be known.

Typically, in combat situations, penetration trauma and amputations are mostly due to explosives. Explosives account for approximately 74% of all battle injuries. Accordingly, an improvised explosive device (IED) is considered a major threat to deployed military personnel. Explosive events cause a blast wave. A blast wave is a high air pressure spike over a short period of time. Thus, in some embodiments, wearable system 100 performs pressure sensing. Determination of a blast wave, indicative of an explosive event, may be based on a combination of, e.g., a loss of electrical conductivity in one or more zones, and/or detecting a high-pressure spike sensed by a pressure sensor and processed by impact detection module 110.

Figure 5A:
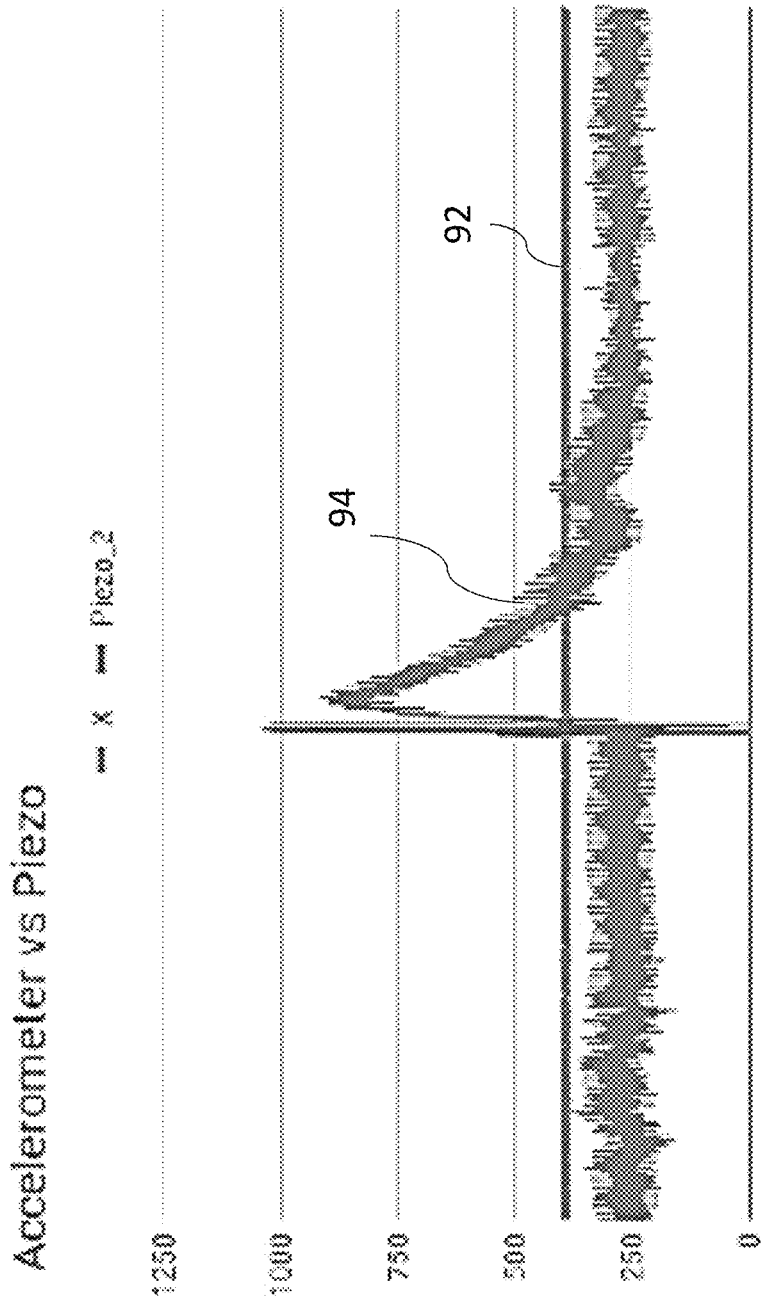
FIGS. 5A-5B are graphs showing sensing of an impact by various types of sensors in accordance with some embodiments of the present invention.
Figure 5B:
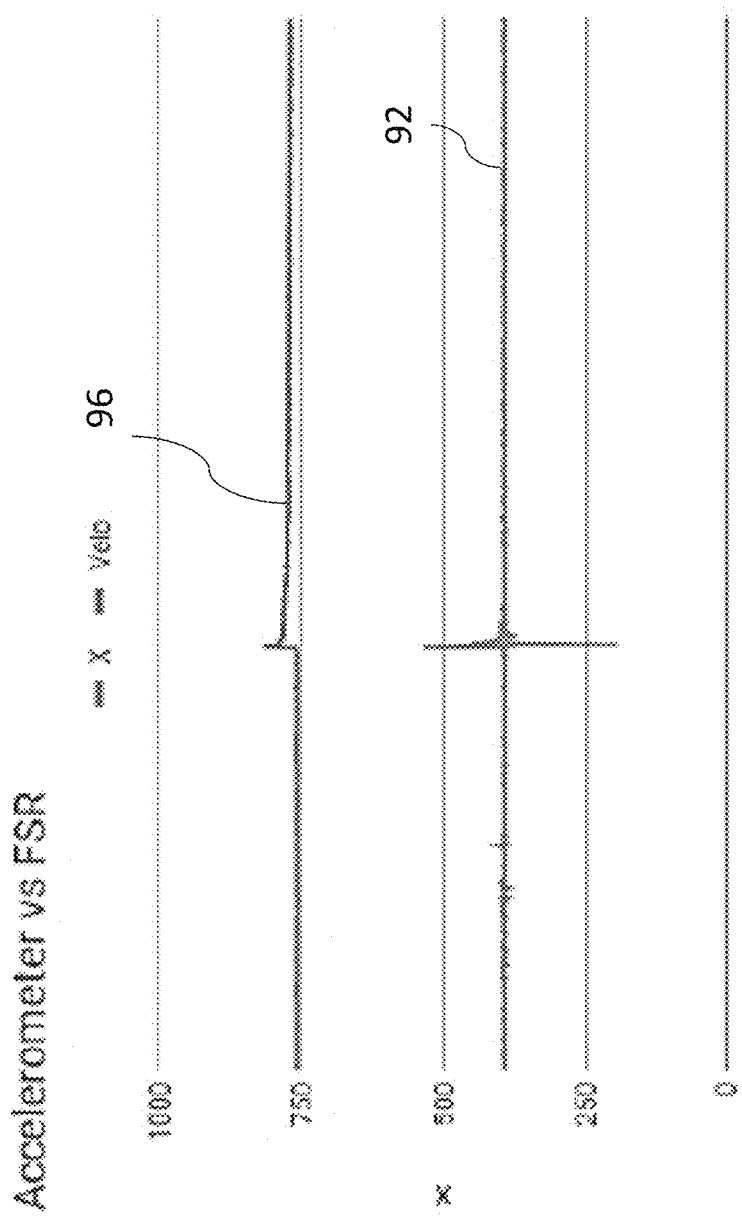

FIGS. 5A-5B are graphs showing measurement associated with an impact as detected by various types of sensors in accordance with some embodiments of the present invention. For example, FIG. 5A is a graph showing sensing of a sudden impact by an accelerometer (indicted by line 92) and a piezo element (indicated by line 94). As shown, both sensors exhibit a change (a spike) in response to a sensed impact. FIG. 5B is a graph showing sensing of a sudden impact to an accelerometer (indicted by line 92) and to an FSR sensor (indicated by line 96). As shown, both sensors exhibit a change (a spike) in response to a sensed impact.

In some embodiments, sensor data, regardless of sensor type, is represented as a temporal signal or a time series of data points, and data analysis may be based on sampling frequency of the temporal signal. in some embodiments, data analysis according to the present disclosure may comprise data preprocessing and processing stages including, but not limited to, data averaging, data filtering, peak signal detection, outlier detection, and the like. In some embodiments, such data analyses may be performed by such data analyses may be performed by impact detection module 110.

In some embodiments, in order to trigger sensing of an event, a plurality of criteria for the event may be predefined. Such criteria may include predetermined thresholds with respect to certain measurable parameters and/or a specified pattern in a data set associated with a certain event. A data pattern may be matched against one or more known data patterns stored in a database, and associated with specific events (e.g., a typical reaction of a specific sensor to an explosion event).

Reference is now made to wearable system 100 as described herein. It is believed by the inventors that by using wearable system 100 in accordance with embodiments of the present invention, a considerable number of lives could be saved during combat situations. By providing accurate information regarding a type and severity of an injury as well as providing post injury response elements, wearable system 100 is configured to be particularly useful for the military. However, wearable system 100 described herein is not limited to use during combat. Wearable system 100 and methods of use thereof are configured for civilian use, as well. For example, wearable system 100 may be used for monitoring people exposed to hazardous occupational and/or environmental conditions, such as law enforcement workers, firefighters, hikers and the like.

Figure 6:
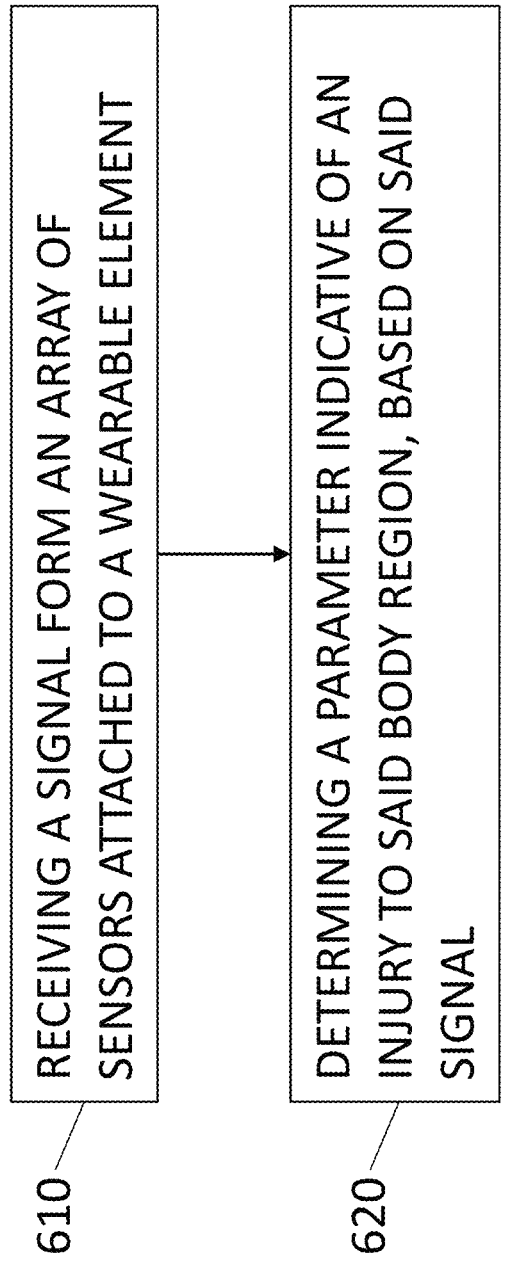
FIG. 6 is a flowchart of a method according to some embodiments of the invention.

Reference is now made to FIG. 6 which is a flowchart of a method 600 of detecting and classifying an injury to said body region. Method 600 may be conducted by injury classification system 100 or by any other computing device. In step 610, a signal may be received form array 120 of sensors attached to wearable element 132. In step 620, detection module 110 may determine a parameter indicative of an injury to said body region, based on said signal.

In some embodiments, method 600 may further include receiving, with respect to said subject, clinical information comprising at least some of: age, sex, temperature, heart rate, blood pressure, and blood oxidation. In some embodiments, the determining is based, at least in part, on said clinical information. In some embodiments, the parameter indicative of said injury comprises a value associated with a severity of the injury.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible system that can retain and store instructions for use by an instruction execution system. The computer readable storage medium may be, for example, but is not limited to, an electronic storage system, a magnetic storage system, an optical storage system, an electromagnetic storage system, a semiconductor storage system, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded system having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing systems from a computer readable storage medium or to an external computer or external storage system via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing system receives computer readable program instructions from the network and forwards the computer readable program instructions for storage in a computer readable storage medium within the respective computing/processing system.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other systems to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other system to cause a series of operational steps to be performed on the computer, other programmable apparatus or other system to produce a computer implemented process, such that the instructions which execute on the computer, other programmable apparatus, or other system implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of a numerical range should be considered to have specifically disclosed all the possible subranges as well as individual numerical values within that range. For example, description of a range from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A wearable system comprising:
   a wearable element designed to be worn on a body region of a subject;
   an array of sensors arranged at specified locations, attached to the wearable element; and
   a detection module in communication with each of said sensors in the array and configured to determine a parameter indicative of an injury to a body region, based on at least one signal generated by at least one of said sensors, wherein the array of sensors is configured to be arranged radially around a limb of said subject, and wherein said detection module is configured to determine said parameter of the injury based on a timing differential in said timing in at least two of said specified locations.

2. The wearable system of claim 1 wherein the parameter indicative of the injury, is at least one of:
   1. an impact event associated with said subject calculated from the signal,
   2. a location of each of said at least one of said sensors relative to said body region, and
   3. a timing of said generating in said signal generated by said at least one sensor.

3. The wearable system of claim 1, wherein said array of sensors is integrated into said wearable element.

4. The wearable system of claim 2, wherein said wearable element is segmented into a plurality of zones, and wherein each of said plurality of zones comprises at least one of said sensors.

5. The wearable system of claim 1, wherein each of said sensors is an electrically conductive element, wherein said signal is indicative of a loss of electrical conductivity in said electrically conductive element at said specified location.

6. The wearable system of claim 5, wherein said loss of conductivity is indicative of a penetration at said specified location.

7. The wearable system of claim 5, wherein the electrically conductive element is one of: a conductive wire embedded in said wearable element, a conductive wire woven into said wearable element, a conductive wire sewn onto said wearable element, conductive ink printed onto said wearable element, conducive glue applied to said wearable element, a conductive sheet, and a conductive mesh.

8. The wearable system of claim 1, wherein said signal is at least one of: a force intensity applied at said specified location; a pressure applied at said specified location; direction-specific acceleration of said body region; linear acceleration of said body region; rotational acceleration of said body region; a movement of said body region; and a penetration of said body region in said specified location.

9. The wearable system of claim 1, wherein said parameter comprises a type of said injury, and wherein the type of injury is one of: blast wave trauma, penetration trauma, and blunt force trauma.

10. The wearable system of claim 9, wherein said injury type is penetration trauma, and said determining further comprises determining at least one of: a dimension of a penetrating object; a velocity of a penetrating object; and a path of a penetrating object within said body region.

11. The wearable system of claim 1, wherein said detection module is configured to receive, with respect to said subject, clinical information comprising at least some of: age, sex, temperature, heart rate, blood pressure, and blood oxidation.

12. The wearable system of claim 11, wherein said determining is based, at least in part, on said clinical information.

13. The wearable system of claim 1, wherein said detection module is configured to operate, with respect to said subject, at least one of an automated tourniquet and an automated drug delivery system, based, at least in part, on said determining.

14. A method comprising:
receiving a signal form an array of sensors attached to a wearable element, wherein each sensor is attached at specified location and wherein the wearable element is designed to be worn on a body region of a subject; and
determining, by a detection module, a parameter indicative of an injury to said body region, based on said signal,
wherein the array of sensors is configured to be arranged radially around a limb of said subject, and wherein said detection module is configured to determine said parameter of the injury based on a timing differential in said timing in at least two of said specified locations.

15. The method of claim 14, wherein the parameter indicative of the injury, is at least one of:

1. an impact event associated with said subject calculated from the signal,
2. a location of each of said at least one of said sensors relative to said body region, and
3. a timing of said generating in said signal generated by said at least one sensor.

16. The method of claim 14, wherein said parameter indicative of said injury comprises a type of said injury and wherein the type of injury is one of: blast wave trauma, penetration trauma, and blunt force trauma.

17. The method of claim 16, wherein said injury type is penetration trauma, and said determining further comprises determining at least one of: a dimension of a penetrating object, a speed of a penetrating object, and a path of a penetrating object within said body region.

18. The method of claim 14, further comprising, receiving, with respect to said subject, clinical information comprising at least some of: age, sex, temperature, heart rate, blood pressure, and blood oxidation.

19. The method of claim 18, wherein said determining is based, at least in part, on said clinical information.

* * * * *